United States Patent [19]

Kees

[11] Patent Number: 5,194,435
[45] Date of Patent: Mar. 16, 1993

[54] 4-ARYLMETHYL-5-ALKYL-3H-PYRAZOL-3-ONES

[75] Inventor: Kenneth L. Kees, Plainsboro, N.J.

[73] Assignee: American Home Products Corporation, New York, N.Y.

[21] Appl. No.: 932,139

[22] Filed: Aug. 19, 1992

Related U.S. Application Data

[63] Continuation-in-part of Ser. No. 864,986, Apr. 7, 1992.

[51] Int. Cl.$^5$ .............. A61K 31/415; A61K 31/495; C07D 403/02; C07D 405/02
[52] U.S. Cl. .................. 514/249; 514/404; 544/353; 548/364.4; 548/364.7; 548/306.1
[58] Field of Search ............ 544/353; 548/364; 514/249, 404

[56] References Cited

FOREIGN PATENT DOCUMENTS 3531658  3/1987  Fed. Rep. of Germany .
2266348 10/1990  Japan .

OTHER PUBLICATIONS

Boots et al., Chemical Abstracts, vol. 67 (1967) No. 32651n.

Primary Examiner—Robert W. Ramsuer
Attorney, Agent, or Firm—Richard K. Jackson

[57] ABSTRACT

The compounds of the formula:

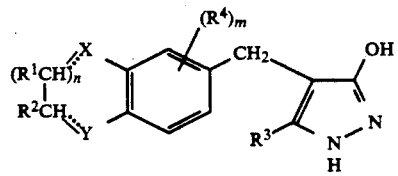

in which the dotted lines represent optional unsaturation when n is 1 or 2 and X is $CR^5$, Y is $CR^6$ or X or Y are N; $R^1$ is hydrogen, alkyl, aryl or arylalkyl; $R^2$ is hydrogen, alkyl, aryl or arylalkyl; $R^3$ is alkyl, perfluoromethyl or alkoxy; $R^4$ is halogen, alkyl or alkoxy; X is $CR^5$, O, S or N, in which $R^5$ is hydrogen, halogen, alkyl, or alkoxy; Y is $CR^6$, O, S or N, in which $R^6$ is hydrogen, halogen, alkyl or alkoxy; n is one of the integers 0, 1 or 2; m is one of the integers 0, 1, 2, or 3; or a pharmaceutically acceptable salt thereof, with the provisos that one of X and Y is O,S or N and $R^3$ is other than alkyl when n and m are 0 and X and Y are O, are useful hypolglycemic agents in the treatment of non-insulin dependent diabetes melitus.

7 Claims, No Drawings

4-ARYLMETHYL-5-ALKYL-3H-PYRAZOL-3-ONES

RELATED APPLICATIONS

This application is a continuation-in-part of U.S. patent application Ser. No. 07/864,986, filed Apr. 7, 1992.

BACKGROUND OF THE INVENTION

French patent application 2529786 discloses a group of 3-phenyl or pyridyl-5-pyrazolone derivatives useful in improving cardiac contractibility (cardiotonics). Japanese patent 55/157504 discloses a group of herbicidal compounds of the formula:

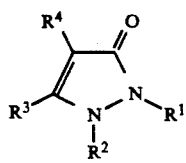

in which $R^1$ is hydrogen or alkyl; $R^2$ is alkyl, alkoxycarbonylmethyl or phenyl; $R^3$ is alkyl; and $R^4$ is hydrogen, alkanoyl, or a substituted or unsubstituted benzyl or benzoyl group. German application 3531658 A1 discloses a very broad genus which embraces certain 2-substituted-5-(4,4-dimethyl-5-oxo-4,5-3-pyrazolyl)indoles (page 12, last line—page 13, line 4) as cardiovascular medications. E.P. 0 125 406 A2 discloses some compounds of the formula:

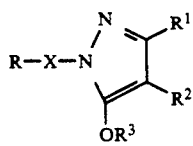

where R is aryl or heteroaryl group and X is alkylene, oxyalkylene or thioalkylene, as lipoxygenase inhibitors. U.S. Pat. No. 3,190,888 discloses some N'-phenoxyalkyl pyrazoles as hypoglycemic agents.

BRIEF DESCRIPTION OF THE INVENTION

This invention provides a group of 4-(heteroarylmethyl)-5-substituted-3-pyrazolone derivatives which have antihyperglycemic properties useful in the treatment of non-insulin dependent diabetes mellitus.

DETAILED DESCRIPTION OF THE INVENTION

In accordance with this invention, there is provided a group of compounds of the formula:

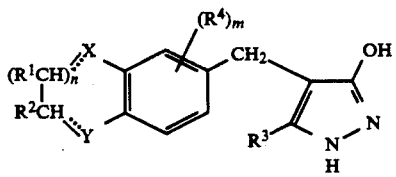

in which
X is $CR^5$, O, S or N, where $R^5$ is hydrogen, halogen, alkyl of 1 to 6 carbon atoms or alkoxy of 1 to 6 carbon atoms;

Y is $CR^6$, O, S or N, where $R^6$ is hydrogen, halogen, alkyl of 1 to 6 carbon atoms or alkoxy of 1 to 6 carbon atoms;
wherein one of X or Y is O, S or N;
n is one of the integers 0, 1 or 2, and the dotted line represents optional unsaturation when n is 1 or 2 and X is $CR^5$ or N, and when Y is $CR^6$ or N;
m is one of the integers 0, 1, 2 or 3;
$R^1$ is hydrogen, alkyl of 1 to 6 carbon atoms, aryl of 6 to 10 carbons or aryalkyl of 7 to 12 carbon atoms;
$R^2$ is hydrogen, alkyl of 1 to 6 carbon atoms, aryl of 6 to 10 carbons or arylalkyl of 7 to 12 carbon atoms;
$R^3$ is alkyl of 1 to 3 carbon atoms, perfluoromethyl or alkoxy of 1 to 6 carbon atoms, with the proviso that, when n is 0 and X and Y are O, $R^3$ is other than alkyl;
$R^4$ is halogen, alkyl or 1 to 6 carbon atoms or alkoxy of 1 to 6 carbon atoms;
or a pharmaceutically acceptable salt thereof., The preferred compounds are those of the formula:

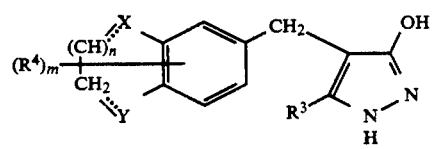

in which
the dotted lines represent optional unsaturation when n is 1 and X is $CR^5$ or N, and when Y is N;
$R^3$ is trifluoromethyl;
$R^4$ is hydrogen or halogen;
X is $CR^5$, O, S or N;
Y is O, S or N;
n is one of the integers 0 or 1;
m is one of the integers 0, 1, 2 or 3;
or a pharmaceutically acceptable salt thereof.

In the compounds disclosed above, the alkyl group representing $R^{1-6}$ are methyl, ethyl, propyl, isopropyl, butyl, tert-butyl, pentyl, hexyl, and the like, the methyl, ethyl, propyl and isopropyl groups being preferred; the aryl groups are phenyl, tolyl, ethylphenyl, xylyl and the like; the arylalkyl groups are benzyl, phenethyl, naphthyl, naphthylmethyl and the like; the alkoxy groups correspond in size to the alkyl groups defined above; and the halogens are chloro, bromo, fluoro and iodo, the first two being preferred. It is preferred that $R^3$ is trifluormethyl.

The pharmaceutically acceptable salts of the compounds of this invention where X and/or Y are nitrogen may be derived from known inorganic and organic acids such as hydrochloric, oxalic, tartaric, fumaric, lactic, phosphoric, p-toluene sulfonic, formic, hydrobromic, maleic, sulfamic acids, and the like. Where X and Y are carbon, oxygen or sulfur, salts of the pyrazolone with bases are readily formed. Suitable cations are the alkali metals (Na or K) the alkaline earth metals (Mg or Ca), ammonium or primary or secondary alkyl amines.

The compounds of this invention are prepared conventionally by the reaction of:

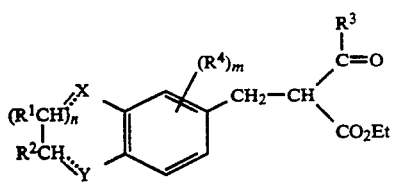

with hydrazine.

The following examples illustrate the preparation of representative compounds of this invention. The compounds are named as 3H-pyrazol-3-one derivatives although it is recognized that this may occur in any of the tautomeric forms:

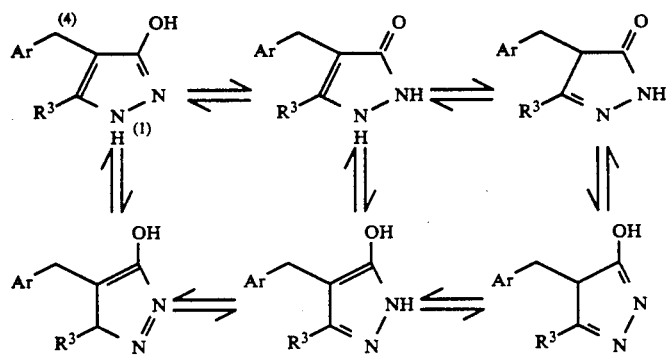

EXAMPLE 1

1,2-Dihydro-4-[(6-quinoxalinyl)methyl]-5-(trifluoromethyl)-3H-pyrazol-3-one

A mixture of sodium hydride (3.5 g, 60% oil dispersion) and 1,2-dimethoxyethane (125 mL) were cooled in ice under a nitrogen atmosphere. Ethyl 4,4,4-trifluoroacetoacetate (12 mL) was added dropwise at a rate so as to control hydrogen evolution. The reaction mixture was then warmed to reflux temperature and a solution of 6-bromomethylquinoxaline (15.5 g, prepared by bromination of 6-methylquinoxaline [20 g] with N-bromosuccinimide [1.2 eq] in carbon tetrachloride in the presence of a catalytic amount of azo(bis)isobutylnitrile, refluxed under nitrogen for 2 hours) in 125 mL, 1,2-dimethoxyethane was added. The reaction was refluxed 15 hours, volatile materials were removed in vacuo on the rotary evaporator and the residue partitioned between saturated aqueous NaCl solution and ethyl acetate. The organic phase was dried (MgSO$_4$), concentrated and the residue chromatographed on silica gel 60 (40 wt. eq), elution with 1:1 ethyl acetae-hexane+1% acetic acid to give 11 g of ethyl 6-quinoxolinyl-α-(trifluoroacetyl)-propanoate.

A mixture of the above β-keto ester (5.5 g) and anhydrous hydrazine (0.78 mL) in 300 mL of toluene were combined at 0° C. for 1 hour then brought to reflux for 48 hours. The reaction mixture was cooled and volatile materials removed on a rotary evaporator. The residue was partitioned between ethyl acetate and 5N HCl solution. The organic phase was washed with saturated aqueous NaCl solution, dried over MgSO$_4$ and concentrated to give 4.3 g of a tan solid. Recrystallization from hot ethanol gave the title compound as tan crystals, m.p. 266°-268° C.

Elemental analysis for: $C_{13}H_9F_3N_4O$; Calc'd: C, 53.07; H, 3.08; N, 19.04. Found: C, 53.17; H, 3.01; N, 19.01.

EXAMPLE 2

4-[1,3-Benzodioxol-5-yl)methyl]-1,2-dihydro-5-(trifluoromethyl)-3H-pyrazol-3-one A mixture of carbon tetrabromide and 1,3-benzodioxol-5-yl)methanol in dichloromethane were cooled in ice under a nitrogen atmosphere. Triphenylphosphine was added as a solid portionwise over about 0.5 hours. The reaction was kept in ice an additional 1.5 hours, then allowed to arm to ambient temperature. The volatile materials were removed in vacuo on the rotary evaporator and the residue dissolved in warm dichloromethane and cooled in ice. The off-white precipitate was collected and dried on a vacuum funnel to afford ethyl 6-(1,3-benzodioxol-5-yl)-α-(trifluoroacetyl)propionate.

The title compound was prepared from the β-keto ester and anhydrous hydrazine as in Example 1. The crude point was recrystallized from ethyl acetatehexane mixture which gave off-white crystals, m.p. 196°-197° C.

Elemental analysis for: $C_{12}H_9F_3N_2O_3$; Calc'd: C, 50.36, H, 3.17; N, 9.79. Found: C, 50.43; H, 3.54; N, 9.60.

EXAMPLE 3

4-(Benzo[b]thien-5-yl)methyl-1,2-dihydro-5-(trifluoromethyl)-3H-pyrazol-3-one

A 500 mL three necked flask fitted with a short path distillation apparatus, internal thermometer and a dropping funnel equipped with a teflon tube (protruding to the bottom of the flask) was charged with 100 mL of polyphosphoric acid and a few boiling stones. The entire apparatus was evacuated to 0.25 mmHg and the reaction flask was immersed in an oil bath heated to 170° C. When the internal temperature rose to 170° C., 25 g of 4-methylphenylthioacetaldehyde diethyl acetal was added at a rate so as to a control the internal temperature at 170° C. Pure 5-methylbenzo[b]thiophene (6 g) was collected, distilling at 120° C. (still head temperature).

5-Bromomethylbenzo[b]thiophene was prepared from 5-methylbenzo[b]thiophene and N-bromosuccinimide as in Example 1 except that the reaction was refluxed 15 hours.

The title compound was prepared as in example 1 from the corresponding β-keto ester and anhydrous hydrazine. 1,2-Dimethoxyethane was used as the solvent. The product was recrystallized from diethyl ether-hexane and then from toluene-petroleum ether mixtures to give a yellow powder, m.p. 188°–189° C.

Elemental analysis for: $C_{13}H_9F_3N_2OS \cap 0.0625\ C_7H_8$ (toluene); Calc'd: C, 52.86; H, 3,44; N, 9.18. Found: C, 62.96; H, 3.10; N, 9.18.

EXAMPLE 4

4-[(2,3-Dihydro-1,4-benzodioxin-6-yl)methyl]-1,2-dihydro-5-methyl-3H-pyrazol-3-one 2,3-Dihydro-1,4-benzodioxin-6-carboxyaldehyde (12.5 g), 8.8 mL of ethyl acetoacetate, acetic acid (0.79 mL) and piperidine (0.27 mL) were combined in 250 mL benzene and the mixture heated to reflux with azeotropic removal of water (Dean-Stark trap) for 15 hours. The reaction mixture was cooled to room temperature, volatile materials were removed in vacuo on the rotary evaporator and the residue was partitioned between ethyl acetate and 1N aqueous HCl solution. The organic phase was separated, washed with saturated brine solution, dried over MgSO$_4$ and concentrated. The residue was filtered through a short silica gel pad with the aid of ethyl acetate, concentrated in vacuo and the residue distilled using a kugelrohr apparatus. The produce obtained, α-(acetyl)-3-(2,3-dihydro-1,4-benzodioxin-6-yl)propenoic acid ethyl ester, as a bright yellow oil, a mixture of E and Z double bond isomers, was used directly in the next step.

The E and Z propenoic ester (5 g) mixture was added to a solution of sodium borohydride (2.97 g) in anhydrous pyridine at room temperature. The reaction was stirred at room temperature for 24 hours. Pyridine was removed in vacuo on the rotary evaporator and the residue was triturated with dichloromethane. The dichloromethane solution was decanted into ice cold 0.5 N HCl solution. The organic phase was separated and washed with saturated aqueous NaCl solution, dried over MgSO$_4$ and concentrated to give 5 g of pure α-(acetyl)-3-(2,3-dihydro-1,4-benzodioxin-6-yl)propanoic acid ethyl ester as a colorless oil.

The title compound was prepared from the above β-keto ester and anhydrous hydrazine in ethanol according to Example 1. The product precipitated from the ethanol and was collected on a suction funnel, washed with ethyl acetate and diethyl ether and air dried. The white solid decomposed at 254°–256° C.

Elemental analysis for: $C_{13}H_{14}N_2O_3$; Calc'd: C, 63.40; H, 5.73; N, 11.37. Found: C, 63.34; H, 5.74; N, 11.61.

The antihyperglycemic activity of the compounds of this invention was established by subjecting them to the following standard experimental procedure for that purpose:

Two to seven month old, male, db/db mice (35–60 g) are placed in seven groups of four (drug group) to six (vehicle group) mice. The test compound is administered in single oral doses, once a day, for four days. The control group receives vehicle only over the same period. Ciglitazone is employed as a positive control, by gavage administration of 100 mg/kg/day. Food is supplied to the mice ad libitum during the test procedure. On the fourth day, blood plasma glucose levels are determined and compared with the vehicle group. The percent change in plasma glucose levels are determined at each dose to statistical significance of $p<0.05$.

The results of these test are as follows:

TABLE

| Example | % change (glucose) | dose (mg/kg) |
| --- | --- | --- |
| 1 | −27 | 20 |
| 2 | −38 | 20 |
| 3 | −29 | 20 |
| 4 | −21 | 20 |
| Ciglitazone Standard | −33 | 100 |

From the experimental data obtained, it is apparent that the compounds of this invention reduce blood glucose levels, which characterizes them as antihyperglycemic agents useful in the treatment of disease states involving abnormally high blood levels of glucose, such as diabetes mellitus. As such, the compounds of this invention are to be administered to a mammal suffering from excessive blood levels of glucose in an amount from 2 mg to about 100 mg per kilogram body weight, or more, per day, in single or multiple doses. An optimum dosing regiment to achieve the desired therapeutic response must be individualized for the patient by following the post-administration glucose blood levels. The dosage will vary with the compound administered and with the patient's age, weight, severity of disease state, response, etc., as is common in all therapeutic methods of control glucose levels.

The compounds of this invention are orally active and may be made up in conventional unit dosage forms of administration. Compositions with inert diluents or edible carriers are compressed into tablets or filled in hard of soft gelatin capsules, with sufficient active ingredient to supply a daily dose of any fraction thereof. Slow release formulations are especially suitable for control of glucose with the compounds of this invention. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aids binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurized compositions. The active ingredients, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions from parenteral administration.

Liquid pharmaceutical compositions which are sterile solutions or suspensions can be utilized, for example, intramuscular, intraperitoneal or subcutaneous injection. Sterile solutions can also be administered intravenously. When the compound is orally active, it can be administered orally either in liquid or solid composition form.

Preferably the pharmaceutical composition is in unit dosage form, e.g. as tablets or capsules. In such form the composition is sub-divided in unit dose containing appropriate quantities of the active ingredient; the unit dosage forms can be packaged compositions, for example packeted powders, vials, ampoules, prefilled syringes or sachets containing liquids. The unit form can be, for example, a capsule or tablet itself, or it can be the appropriate number of dosage of any such compositions in package form. The quantity of the active ingredient in unit dose of compositions may be varied or adjusted from about 2 mg or less to 100 mg or more, according to the particular need and the activity of the active ingredient. The invention also includes the compounds in the absence of the carrier where the compounds are in unit dosage form.

What is claimed is:

1. A compound of the formula:

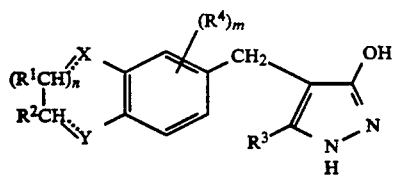

in which
X is $CR^5$, O, S or N, where $R^5$ is hydrogen, halogen, alkyl of 1 to 6 carbon atoms or alkoxy of 1 to 6 carbon atoms;
Y is O, S or N;
n is one of the integers 0, 1 or 2; with the provisos that:
a) when n is 0, X is $CR^5$, O or S and Y is O or S, and when X is $CR^5$, the dotted line to X represents unsaturation, and when X and Y are O, $R^3$ is other than alkyl; and
b) when n is 1 or 2 and X is $CR^5$ or N the dotted line to X represents unsaturation and when Y is N the dotted line to Y represents unsaturation;
m is one of the integers 0, 1, 2 or 3;
$R^1$ is hydrogen, alkyl of 1 to 6 carbon atoms, aryl of 6 to 10 carbon atoms or arylalkyl of 7 to 12 carbon atoms;
$R^2$ is hydrogen, alkyl or 1 to 6 carbon atoms, aryl of 6 to 10 carbon atoms or arylalkyl of 7 to 12 carbon atoms;
$R^3$ is alkyl of 1 to 3 carbon atoms, perfluoromethyl or alkoxy of 1 to 6 carbon atoms;
$R^4$ is halogen, alkyl of 1 to 6 carbon atoms or alkoxy of 1 to 6 carbon atoms;
or a pharmaceutically acceptable salt thereof.

2. A compound of claim 1 in which
$R^3$ is trifluoromethyl;
$R^4$ is a halogen; and
n is one of the integers 0 or 1;
or a pharmaceutically acceptable salt thereof.

3. A compound of claim 1 which is 1,2-dihydro-4-[(6-quinoxalinyl)methyl]-5-(trifluoromethyl)-3H-pyrazol-3-one, or a pharmaceutically acceptable salt thereof.

4. A compound of claim 1 which is 4-[(1,3-benzodioxol-5-yl)methyl]-1,2-dihydro-5-(trifluoromethyl)-3H-pyrazol-3-one, or a pharmaceutically acceptable salt thereof.

5. A compound of claim 1 which is 4-(benzo[b]thien-5-yl)methyl-1,2-dihydro-5-(trifluoromethyl)-3H-pyrazol-3-one, or a pharmaceutically acceptable salt thereof.

6. A compound of claim 1 which is 4-[(2,3-dihydro-1,4-benzodioxin-6-yl)methyl]-1,2-dihydro-5-methyl-3H-pyrazol-3-one, or a pharmaceutically acceptable salt thereof.

7. A process for reducing blood serum glucose levels in a mammal in need thereof which comprises administering to said mammal, orally or parenterally, a hypoglycemic amount of a compound of the formula:

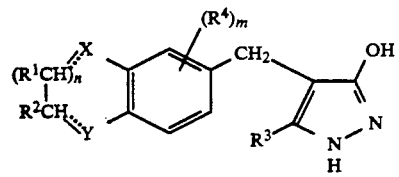

in which
X is $CR^5$, O, S or N, where $R^5$ is hydrogen, halogen, alkyl or 1 to 6 carbon atoms or alkoxy of 1 to 6 carbon atoms;
Y is O, S or N;
n is one of the integers 0, 1 or 2; with the provisos that:
a) when n is O, X is $CR^5$, O or S and Y is O or S, and when X is $CR^5$, the dotted line to X represents unsaturation, and when X and Y are O, $R^3$ is other than alkyl; and
b) when n is 1 or 2 and X is $CR^5$ or N the dotted line to X represents unsaturation and when Y is N the dotted line to Y represents unsaturation;
m is one of the integers 0, 1, 2 or 3;
$R^1$ is hydrogen, alkyl of 1 to 6 carbon atoms, aryl of 6 to 10 carbon atoms or arylalkyl of 7 to 12 carbon atoms;
$R^2$ is hydrogen, alkyl of 1 to 6 carbon atoms, aryl of 6 to 10 carbon atoms or arylalkyl of 7 to 12 carbon atoms;
$R^3$ is alkyl of 1 to 3 carbon atoms, perfluoromethyl or alkoxy of 1 to 6 carbon atoms;
$R^4$ is halogen, alkyl of 1 to 6 carbon atoms or alkoxy of 1 to 6 carbon atoms;
or a pharmaceutically acceptable salt thereof.

* * * * *